United States Patent [19]

Ueda et al.

[11] Patent Number: 4,564,472
[45] Date of Patent: Jan. 14, 1986

[54] 3-AMINOMETHYLENE-2,4-PENTANEDIONE BIS(THIOSEMICARBAZONE) DERIVATIVES, AND THEIR PRODUCTION AND USE

[75] Inventors: Nobuo Ueda, Kawanishi; Susumu Kondo; Masaaki Hazue, both of Hyogo, all of Japan

[73] Assignee: Nihon Medi-Physics Co., Ltd., Hyogo, Japan

[21] Appl. No.: 509,669

[22] Filed: Jun. 30, 1983

Related U.S. Application Data

[62] Division of Ser. No. 332,152, Dec. 18, 1981.

[30] Foreign Application Priority Data

Dec. 19, 1980 [JP] Japan ................... 55-180770
Dec. 19, 1980 [JP] Japan ................... 55-180771

[51] Int. Cl.⁴ .................... C07G 7/04; C07G 7/00
[52] U.S. Cl. .................... 260/113; 260/112 R; 260/112.5 R; 260/121; 424/1.1; 435/188; 435/215; 562/556
[58] Field of Search ........... 260/112 R, 121, 113, 260/112.5 R; 455/215, 188; 424/1.1, 323; 562/556

[56] References Cited

U.S. PATENT DOCUMENTS

| 3,382,275 | 5/1968 | Barrett | 564/20 X |
| 3,709,935 | 1/1973 | Barrett | 564/19 |
| 3,824,276 | 7/1974 | Murray et al. | 564/19 X |
| 4,287,362 | 9/1981 | Yokoyama et al. | 424/1.1 X |
| 4,338,248 | 7/1982 | Yokoyama et al. | 260/121 X |

FOREIGN PATENT DOCUMENTS

| 54920 | 6/1982 | European Pat. Off. | 424/1.1 |
| 74429 | 3/1983 | European Pat. Off. | 424/1.1 |
| 966849 | 8/1964 | United Kingdom | 424/323 |
| 356274 | 11/1972 | U.S.S.R. | 564/19 |

OTHER PUBLICATIONS

Polonovski et al., Comptes Rend. 232, 1260–1262, 1951.
J. of Nucl. Med., vol. 17, No. 9, 816–819, (1976), Yokoyama et al.
Yakugaku Zasshi, 97, pp. 671–675, (1977), Nishimura et al.

Primary Examiner—Howard E. Schain
Attorney, Agent, or Firm—Birch, Stewart, Kolasch & Birch

[57] ABSTRACT

A radioactive diagnostic agent which comprises a physiologically active substance and a radioactive metallic element combined with a compound of the formula:

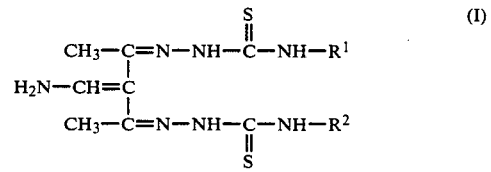

wherein $R^1$ and $R^2$ are each hydrogen, $C_1$–$C_3$ alkyl or phenyl. The agent is characteristic in having a high stability even after being administered into a human body and showing the substantially the same behavior as the physiologically active substance itself in a human body.

19 Claims, No Drawings

3-AMINOMETHYLENE-2,4-PENTANEDIONE BIS(THIOSEMICARBAZONE) DERIVATIVES, AND THEIR PRODUCTION AND USE

This application is a divisional of copending application Ser. No. 332,152, filed on Dec. 18, 1981.

The present invention relates to 3-aminomethylene-2,4-pentanedione bis(thiosemicarbazone) derivatives, and their production and use. More particularly, it relates to 3-aminomethylene-2,4-pentanedione bis(thiosemicarbazone) derivatives (hereinafter referred to as "BTS") of the formula:

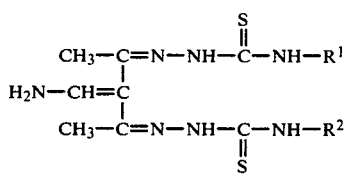

wherein $R^1$ and $R^2$ are each a hydrogen atom, a $C_1$–$C_3$ alkyl group or a phenyl group, their production process and their use as a carrier for a radioactive metallic element as well a physiologically active substance.

For the purpose of a non-invading nuclear medical diagnosis such as recording, dynamic study and quantitative measurement of the blood circulation system, detection of physiological abnormality or localization of abnormality by imaging, there have been widely used physiologically active substances labeled with iodine-131 ($^{131}I$) such as $^{131}I$-labeled serum albumin and $^{131}I$-labeled fibrinogen. However, $^{131}I$ has a long half life of about 8 days and emits beta-rays so that the patient administered therewith is exposed to a large quantity of radiation.

In order to overcome the said drawback in the $^{131}I$-labeled physiologically active substances, attempts have been made to provide radioactive diagnostic agents comprising physiologically active substances and radioactive metallic elements having more favorable physical properties than iodine-131 combined thereto. Among such attempts, there is known a labeling method wherein a physiologically active substance is treated directly with a radioactive metal salt to make a chelate compound, which may be used as a radioactive diagnostic agent. For instance, human serum albumin is treated with an aqueous solution containing technetium-99m ($^{99m}Tc$) in the form of pertechnetate in the presence of a reducing agent to give $^{99m}Tc$-labeled human serum albumin. Further, for instance, bleomycin is treated with an aqueous solution containing indium-111 ($^{111}In$) in the form of indium chloride to give $^{111}In$-labeled bleomycin. However, the chelate forming property of those physiologically active substances is not sufficient, and the once formed chelating bond is readily broken. In fact, $^{99m}Tc$-labeled serum albumin and $^{111}In$-labeled bleomycin are low in the stability after administration into living bodies so that the behavior of the radioactivity in such bodies does not coincide with that of serum albumin or bleomycin as the physiologically active substance. This is a fatal defect for the nuclear medical diagnosis based on the exact trace of the behavior of the radioactivity which should coincide with the behavior of the physiologically active substance.

As a result of the extensive study, it has now been found that the BTS (I) has a strong chelate-forming property and can be bonded to an amino group and/or a carboxyl group in physiologically active substances under a mild condition. It has also been found that a chemical product comprising a physiologically active substance and a radioactive metallic element bonded thereto with intervention of the BTS (I) is sufficiently stable in living bodies, and the behavior of the radioactivity in living bodies is quite coincident with that of the physiologically active substance itself.

According to the present invention, there is provided the BTS (I), which is useful as a chemical carrier for a physiologically active substance and a radioactive metallic element. There is also provided the physiologically active substance-combined BTS (I) comprising the BTS (I) and a physiologically active substance chemically bonded thereto with or without intervention of any linking aid, which is useful as a non-radioactive carrier to be used in diagnosis in nuclear medicine. There is further provided the radioactive metallic element-labeled, physiologically active substance-combined BTS (I) comprising the physiologically active substance-combined BTS (I) and a radioactive metallic element chelated thereto, which is useful as a radioactive diagnostic agent.

The BTS (I) is novel and can be produced by condensing 3-aminomethylene-2,4-pentadione (A. Kreutzberger et al.: J.Org.Chem., 26, 1121 (1961); K. R. Huffman et al.: J.Org.Chem., 27, 551 (1962)) with 4-R-thiosemicarbazide (wherein R is the same as $R^1$ and $R^2$). The condensation may be carried out in a single step or in two steps. When the BTS (I) wherein $R^1$ and $R^2$ are same is to be produced, the condensation is usually carried out in a single step by reacting 3-aminomethylene-2,4-pentadione with 4-R-thiosemicarbazide in a molar proportion of 1:2 or more. When the BTS (I) wherein $R^1$ and $R^2$ are different is to be produced, the condensation is ordinarily carried out in two steps by reactig 3-aminomethylene-2,4-pentadione with 4-$R^1$-thiosemicarbazide in a nearly equimolar proportion and then reacting the resultant monothiosemicarbazone with 4-$R^2$-thiosemicarbazide in a nearly equimolar proportion. In general, the condensation is effected in the presence of an acidic catalyst such as hydrochloric acid, hydrobromic acid or sulfuric acid, preferably in an inert solvent such as methanol or ethanol.

The BTS (I) thus produced has two thiosemicarbazone groups which can catch a radioactive metallic element to form a chelate and an amino group which can be bonded to a carboxyl group or an amino group in a physiologically active substance with or without intervention of any linking aid under a mild condition to fix such physiologically active substance firmly. Therefore, it is useful as a carrier for the radioactive metallic element and the physiologically active substance.

For manufacture of the radioactive diagnostic agent of the present invention, the BTS (I) is usually first combined with a physiologically active substance, and then the resultant combined product is labeled with a radioactive metallic element.

The term "physiologically active substance" is intended to mean any substance which can show a specific accumulability at a certain organ or tissue or a certain diseased locus or exhibits a specific behavior corresponding to a certain physiological state. Tracing of its behavior in a living body can provide informations useful for diagnosis. Such physiologically active substance as having a carboxyl group or an amino group is usable advantageously in this invention. Even when a carboxyl group or an amino group is not present, it may be used by introducing previously a carboxyl group or an amino group therein. Specific examples of the physiologically active substance are blood proteins (e.g. human serum albumin, fibrinogen), enzymes (e.g. urokinase, streptokinase), hormones (e.g. thyroid stimulating hormone, parathyroid hormone), immune antibodies (e.g. IgG), antibiotics (e.g. bleomycin, kanamycin), saccharides, fatty acids, amino acids, etc.

The combination of the BTS (I) with a physiologically active substance may be carried out according to any procedure as conventionally adopted for linking an amino group with a carboxyl group or an amino group. Examples of such procedure include the carbodiimide process, the glutaraldehyde process, etc. According to the carbodiimide process, the BTS (I) having an amino group and a physiologically active substance having a carboxyl group are condensed in the presence of a carbodiimide such as 1-cyclohexyl-3-(2-morpholinyl-4-ethyl)carbodiimide or 1-ethyl-3-(3-dimethylaminopropyl)carbodiimide to form a carbonamide linkage between the amino group and the carboxyl group. According to the glutaraldehyde process, the BTS (I) having an amino group and a physiologically active substance having an amino group are reacted in the presence of glutaraldehyde as a linking aid, and the resultant Schiff base is reduced with a reducing agent such as sodium borohydride. In the resulting products, two amino groups are combined with intervention of a pentamethylene linkage. These bonding procedures are quite advantageous in accomplishment of the bonding under a mild condition so that any inactivation, denaturation or decomposition of the physiologically active substance does not materially take place.

When desired, the thus prepared physiologically active substance-combined (hereinafter referred to as "PAS-combined") BTS (I) may be purified by a per se conventional procedure such as dialysis, gel filtration or column chromatography so as to eliminate impurities such as unreacted reagents therefrom. As the result, the combined product is usually obtained in the form of an aqueous solution, and this aqueous solution may be as such used for labeling with a radioactive metallic element. Alternatively, the aqueous solution may be subjected to lyophilization, evaporation under reduced pressure at low temperatures or the like to obtain a dried product, which also can be used as such or in the form of solution for labeling. Depending on the use, the said aqueous solution or the said dried product may be incorporated with any additive such as a pH controlling agent (e.g. an acid, a base, a buffer), a stabilizer (e.g. ascorbic acid), an isotonizing agent (e.g. sodium chloride) or a preserving agent (e.g. benzyl alcohol). In addition, the said aqueous solution or the said dried product may contain any reducing or oxidizing agent, which will act on a radioactive metallic element to be labeled so as to give a stable chelate product, as hereinafter explained. Still, the PAS-combined BTS (I) is per se quite stable and can be readily labeled with a radioactive metallic element by a simple procedure as hereinafter explained, and therefore it may be stored and supplied on the demand so that its production from the BTS (I) and the physiologically active substance can be saved from the practitioner such as a medical doctor.

For the labeling of the PAS-combined BTS (I) as the non-radioactive carrier with a radioactive metallic element, the PAS-combined BTS (I) may be treated with the radioactive metallic element in an appropriate form.

The term "radioactive metallic element" is intended to mean any metallic element having radioactivity, which has physical characteristics suitable for nuclear medical diagnosis. Specific examples of the radioactive metallic element are gallium-67 ($^{67}$Ga), gallium-68 ($^{68}$Ga), thallium-201 ($^{201}$Tl), $^{111}$In, $^{99m}$Tc, etc. They are normally employed in their salt forms, particularly in their watersoluble salt forms.

Depending upon the kind or state of the radioactive metallic element, there may be adopted two different labeling manners. When the radioactive metallic element is in a valency state which is not required to be reduced or oxidized for formation of a stable chelate compound, the PAS-combined BTS (I) is contacted with the radioactive metallic element in an aqueous medium to obtain the radioactive metallic element-labeled, PAS-combined BTS (I). This labeling manner may be applied to $^{67}$Ga, $^{111}$In, etc. When the radioactive metallic element is in a valency state which is required to be reduced or oxidized for formation of a stable chelate compound, the PAS-combined BTS (I) is contacted with the radioactive metallic element in an aqueous medium in the presence of a reducing agent or an oxidizing agent to obtain the radioactive metallic element-labeled, PAS-combined BTS (I). This labeling manner may be applied to $^{99m}$Tc, etc.

As the reducing agent, there may be usually employed a stannous salt, i.e. a salt of divalent tin ion ($Sn^{++}$). Specific examples are stannous halides (e.g. stannous chloride, stannous fluoride), stannous sulfate, stannous nitrate, stannous acetate, stannous citrate, etc. $Sn^{++}$ ion-bearing resins such as ion-exchange resins charged with $Sn^{++}$ ion are also usable.

When, for instance, the radioactive metallic element is $^{99m}$Tc, the PAS-combined BTS (I) may be treated with $^{99m}$Tc in the form of pertechnetate in an aqueous medium in the presence of a reducing agent such as a stannous salt. As to the order of the introduction of the above reagents into the reaction system, any particular limitation does not exist. Usually, however, the mixing of the stannous salt with the pertechnetate in an aqueous medium in the first place should be avoided. The stannous salt may be used in such an amount as can reduce sufficiently the pertechnetate.

The radioactive diagnostic agent should have sufficient radioactivity and radioactivity concentration which can assure reliable diagnosis. For instance, in case of the radioactive metallic element being $^{99m}$Tc, it may be included usually in an amount of 0.1 to 50 mCi in about 0.5 to 5.0 ml at the time of administration. The amount of the PAS-combined BTS (I) may be such as sufficient to form a stable chelate compound with the radioactive metallic element.

The thus produced radioactive metallic element-labeled, PAS-combined BTS (I) as the radioactive diagostic agent is sufficiently stable, and therefore it may be stored as such and supplied on the demand. When desired, the radioactive diagnostic agent may contain any additive such as a pH controlling agent (e.g. an acid, a base, a buffer), a stabilizer (e.g. ascorbic acid) or an isotonizing agent (e.g. sodium chloride).

The radioactive metallic element-labeled, PAS-combined BTS (I) of this invention is useful for nuclear medical diagnosis. For instance, $^{99m}$Tc-labeled, human serum albumin-combined BTS (I) can be used for recording, dynamic study and quantitative measurement of the blood circulation system by administering intravenously to a human body. Further, for instance, $^{99m}$Tc-labeled, fibrinogen-combined BTS (I) or $^{99m}$Tc-labeled, urokinase-combined BTS (I) may be used for detection and recording of thrombosis as well as localization of thrombosis, since they accumulate at the locus of thrombosis. Further, for instance, $^{99m}$Tc-labeled, streptokinase-combined BTS (I) is useful for determination of the locus of myocardial infarction. Moreover, for instance, $^{99m}$Tc-labeled, thyroid stimulating hormone-combined BTS (I) is useful for detection and recording of a cancer at the thyroid gland.

The radioactive diagnostic agent of this invention may be administered to patients in an amount sufficient to produce a radioactivity necessary for examination of the organ or tissue by an appropriate route, usually through an intravenous route. For instance, the intravenous administration of a $^{99m}$Tc-labeled radioactive diagnostic agent of about 1 to 3 ml in volume having a radioactivity of about 1 to 20 mCi to a patient is quite suitable for the diagnostic purpose.

The advantages of the PAS-combined BTS (I) as a non-radioactive carrier may be summarized as follows: (a) it is stable over a long period of time after manufacture; (b) since it can be produced under a mild condition, any unfavorable side reaction such as inactivation, denaturation or decomposition is not materially caused to the physiologically active substance; (c) any physiologically active substance having a carboxyl group or an amino group is usable as the starting material; (d) even when a carboxyl group or an amino group is not present, the introduction of such group into a physiologically active substance makes it usable as the starting material; (e) by such a simple procedure as contacting with a radioactive metallic element in an aqueous medium, it can afford a radioactive metallic element-labeled, PAS-combined BTS (I). Likewise, the advantages of the radioactive metallic element-labeled, PAS-combined BTS (I) as a radioactive diagnostic agent may be summarized as follows: (a) it is stable over a long period of time after manufacture; (b) the labeling efficiency with the radioactive metallic element is extremely high (nearly 100 %); (c) since the labeling operation is quite simple, any unfavorable side reaction such as inactivation, denaturation or decomposition is not caused to the physiologically active substance bonded to the BTS (I); (d) among various radioactive metallic elements, the most suitable one for the diagnostic purpose may be chosen and used so that the informations for diagnosis is enhanced not only in quantity but also in quality with reduction of the exposure dose.

Practical and presently preferred embodiments of the invention are illustratively shown in the following Examples wherein % is by weight, unless otherwise defined.

EXAMPLE 1

Production of 3-aminomethylene-2,4-pentanedione bis(N-methylthiosemicarbazone) (hereinafter referred to as "BMTS"):

A solution of syn-triazine (1 g; 12.3 mmol) in acetylacetone (9.3 g; 92.5 mmol) was heated at 155° C. for about 30 minutes. The reaction mixture was cooled to room temperature, whereby pale orange crystals precipitated. The crystals were collected by filtration. The filtrate was concentrated and allowed to stand at room temperature, whereby additional crystals precipitated. The additional crystals were collected by filtration, combined with the previously collected crystals and recrystallized from methanol to give 3-aminomethylene-2,4-pentanedione (2.96 g). M.P., 146° C.

3-Aminomethylene-2,4-pentanedione (530 mg; 4.2 mmol) as above obtained and 4-methylthiosemicarbazide (888 mg; 8.5 mmol) were dissolved in methanol (300 ml), 12 N hydrochloric acid (0.3 ml) was added thereto, and the resultant mixture was heated at 40° C. while stirring for 7 to 8 hours. The precipitated crystals were collected by filtration and recrystallized from methanol to give BMTS (493 mg). M.P., 239° C. (decomp.).

Anal. Calcd. for $C_{10}H_{19}N_7S_2$: C, 39.85%; H, 6.35% N, 32.53%; S, 21.27%. Found: C, 40.16%; H, 5.80%; N, 31.61%; S, 21.50%.

EXAMPLE 2

Production of 3-aminomethylene-2,4-pentanedione bis(N-ethylthiosemicarbazone) (hereinafter referred to as "BETS"):

In the same manner as in Example 1 but using 4-ethylthiosemicarbazide in place of 4-methylthiosemicarbazide, there was produced BETS.

EXAMPLE 3

Preparation of human serum albumin-combined BMTS as a non-radioactive carrier:

On an ice bath, human serum albumin (lyophilized; 75 mg) was dissolved in water (5 ml) to give the solution (A). Separately, BMTS was dissolved in dimethylformamide to make a concentration of 4 mg/ml. To 0.5 ml of the resultant solution, the solution (A) was added, and the resultant mixture was adjusted with 0.1 N hydrochloric acid to a pH of about 4.6 to give the solution (B). An aqueous solution of 1-ethyl-3-(3-dimethylaminopropyl)carbodiimide hydrochloride (10 mg/ml; 1.27 ml) was added to the solution (B) and adjusted with 0.1 N hydrochloric acid to a pH of 4.6, followed by stirring at a temperature below 5° C. for about 15 hours. The resulting mixture was admitted in a dialyzing tube and subjected to dialysis in a conventional manner for 24 hours, followed by centrifugation and lyophilization to give the human serum albumin-combined BMTS as white cotton-like crystals. The crystals (67 mg) were dissolved in 0.2 M acetate buffer (pH, 2.64; 5 ml) as previously eliminated dissolved oxygen therefrom, and 0.1 mM aqueous solution of stannous chloride (2.0 ml) and ascorbic acid (1.18 mg) were added thereto. The resultant solution was passed through a filter having a pore size of 0.22 μm, and 1.5 ml of the filtrate were filled in a vial, of which the inside was flushed with nitrogen, to obtain a non-radioactive carrier as a slightly pale yellow, transparent solution. The above operations were effected under sterile conditions.

EXAMPLE 4

Preparation of human serum albumin-combined BETS as a non-radioactive carrier:

BETS (4 mg) was dissolved in dimethylformamide (2 ml), an equimolar amount of glutaraldehyde (25 % solution) to BETS was added thereto, and the resultant mixture was stirred at room temperature for 15 minutes to make the solution (A). Separately, human serum albumin (lyophilized; 90 mg) was dissolved in 0.01 M phosphate buffer-0.15 M sodium chloride solution (pH, 7.4; 10 ml) to make the solution (B). At a temperature of 0 to 4° C., the solution (A) (1.0 ml) was added to the solution (B), and the resultant mixture was stirred at the same temperature as above for about 1 hour. After addition of sodium borohydride (1 mg), stirring was continued at a temperature of 0 to 4° C. for about 1 hour, whereby reduction proceeded. The resultant mixture was admitted in a dialyzing tube and subjected to dialysis in a conventional manner for 24 hours. The resulting solution was passed through a filter having a pore size of 0.22 μm, and 1.0 ml of the filtrate was filled in a vial, followed by lyophilization to obtain a non-radioactive carrier. The above operations were effected under sterile conditions.

When dissolved in water, the non-radioactive carrier gave a slightly pale yellow, transparent solution.

EXAMPLE 5

Preparation of urokinase-combined BMTS as a non-radioactive carrier:

On an ice bath, purified urokinase (lyophilized; 60 mg) was dissolved in water (5 ml) to give the solution (A). Separately, BMTS was dissolved in dimethylformamide to make a concentration of 4 mg/ml. To 0.5 ml of the resultant solution, the solution (A) was added, and the pH was adjusted with 0.1 N hydrochloric acid to about 4.6 to make the solution (B). To the solution (B), an aqueous solution of 1-cyclohexyl-3-(2-morpholinyl-4-ethyl)carbodiimide (50 mg/ml; 1.5 ml) was added, and the resultant mixture was adjusted with 0.1 N hydrochloric acid to a pH of about 4.6, followed by stirring at a temperature below 5° C. for about 3 hours. The reaction mixture was chromatographed on Sephadex G-50 and eluted with 0.01 M phosphate buffer-0.15 M sodium chloride solution (pH, 7.4). The eluate was diluted with 0.01 M phosphate-0.15 M sodium chloride solution to make a concentration of 5.0 mg/ml of urokinase. The dilution was passed through a filter having a pore size of 0.22 μm, and 1.5 ml of the filtrate were filled in a vial to obtain a non-radioactive carrier as a slightly pale yellow transparent solution. The above operations were effected under sterile conditions.

EXAMPLE 6

Preparation of $^{99m}$Tc-labeled, human serum albumin-combined BMTS as a radioactive diagnostic agent:

The human serum albumin-combined BMTS (solution) obtained in Example 3 (1.5 ml) was admixed with a physiological saline solution (0.5 ml) containing $^{99m}$Tc (15 mCi) in the form of pertechnetate, followed by stirring to give an aqueous solution containing the $^{99m}$Tc-labeled, human serum albumin-combined BMTS useful as a radioactive diagnostic agent. This solution was pale yellow, transparent and had around pH 3.2.

EXAMPLE 7

Preparation of $^{67}$Ga-labeled, human serum albumin-combined BETS as a radioactive diagnostic agent:

The human serum albumin-combined BETS (lyophilized powder) obtained in Example 4 was dissolved in 0.2 M acetate buffer (pH, 4.0; 1.5 ml), and 0.01 N hydrochloric acid (0.5 ml) containing $^{67}$Ga (2 mCi) in the form of gallium chloride was added thereto to give an aqueous solution containing the $^{67}$Ga-labeled, human serum albumin-combined BETS useful as a radioactive diagnostic agent. This solution was slightly pale yellow, transparent and had around pH 3.7.

EXAMPLE 8

Preparation of $^{111}$In-labeled, urokinase-combined BMTS as a radioactive diagnostic agent:

The urokinase-combined BMTS (solution) obtained in Example 5 (1.5 ml) was admixed with 0.1 N hydrochloric acid (0.5 ml) containing $^{111}$In (0.5 mCi) in the form of indium chloride to give an aqueous solution containing the $^{111}$In-labeled, urokinase-combined BMTS useful as a radioactive diagnostic agent. This solution was slightly pale yellow, transparent and had around pH 6.0.

EXAMPLE 9

Properties of $^{99m}$Tc-labeled, human serum albumin-combined BMTS:

In order to examine the labeling efficiency of the $^{99m}$Tc-labeled, human serum albumin-combined BMTS obtained in Example 6, its aqueous solution was subjected to thin layer chromatography using silica gel as a retention material and methylethylketone or 85 % methanol as a developing solvent, and scanning was carried out by the use of a radiochromato-scanner. Irrespective of the kind of the developing solvent, the radioactivity was recorded as a single peak at the original point. Any peak due to a radioactive impurity such as free pertechnetate ion (Rf=1.0 in case of using methylethylketone; Rf=0.8 - 0.9 in case of using 85 % methanol) was not recognized.

Then, the $^{99m}$Tc-labeled, human serum albumin-combined BMTS obtained in Example 6 was subjected to electrophoresis (1.7 mA/cm; 15 minutes) using a Veronal-Veronal Na solution (pH 8.6) as a developing solvent and a cellulose acetate membrane as an electrophoretic membrane, and scanning was effected by the use of a radiochromato-scanner. The radioactivity was recognized as a single peak at the locus 1.8 cm distant from the original line to the positive side. This locus was the same as that of the coloring band of human serum albumin with Ponceau 3R.

From the above results, it may be said that the $^{99m}$Tc-labeled, human serum albumin-combined BMTS obtained in Example 6 has a labeling efficiency of nearly 100 %, and its electric charge is substantially the same as that of human serum albumin.

EXAMPLE 10

Behaviors of $^{99m}$Tc-labeled, human serum albumin-combined BMTS in rabbits:

The $^{99m}$Tc-labeled, human serum albumin-combined BMTS obtained in Example 6 (0.3 ml) was administered intravenously to each of rabbits having a bypass formed by a cannula at the carotid artery through the ear vein, and the variation of the blood level with the lapse of time was examined by measurement of the radioactivity at the bypass.

The results are shown in Table 1 wherein the blood level at each measuring time (with correction for physical attenuation of $^{99m}$Tc) is indicated by a relative value (in average) to that immediately after the administration which is taken as 1.0.

TABLE 1

| Variation of blood level in rabbits | | | | | | |
|---|---|---|---|---|---|---|
| Time after administration (hours) | 0 | 0.25 | 0.5 | 1 | 2 | 3 |
| Relative value | 1.0 | 0.96 | 0.90 | 0.80 | 0.68 | 0.62 |

EXAMPLE 11

Behaviors of $^{99m}$Tc-labeled, human serum albumin-combined BMTS in rats:

The $^{99m}$Tc-labeled, human serum albumin-combined BMTS obtained in Example 6 (0.1 ml) was administered intravenously to each of female rats of SD strain at the tail vein, and the variation of the blood level with the lapse of time was recorded. For the control, the same examination as above was carried out by the use of conventional $^{99m}$Tc-labeled, human serum albumin and conventional $^{131}$I-labeled, human serum albumin.

The results are shown in Table 2 wherein the blood level at each measuring time is indicated by an absolute value (in average).

TABLE 2

| | Variation of blood level in rats (%/g) | | | | |
|---|---|---|---|---|---|
| | Time after administration (hours) | | | | |
| Agent tested | 0.25 | 0.5 | 1 | 2 | 3 |
| $^{99m}$Tc-labeled, human serum albumin-combined BMTS | 7.79 | 6.97 | 6.33 | 5.47 | 5.07 |
| Conventional $^{99m}$Tc-labeled, human serum albumin (Commercial product A) | 5.49 | 3.95 | 3.68 | — | 2.51 |
| Conventional $^{99m}$Tc-labeled, human serum albumin (Commercial product B) | 3.78 | 3.15 | 2.16 | — | 1.88 |
| Conventional $^{131}$I-labeled, human serum albumin | 7.01 | 5.93 | 5.64 | — | 4.59 |

The distribution of the $^{99m}$Tc-labeled, human serum albumin-combined BMTS obtained in Example 6 in the organs of rats with the lapse of time was also observed, and the results are shown in Table 3.

TABLE 3

| Distribution of $^{99m}$Tc-labeled, human serum albumin-combined BMTS in organs of rats with lapse of time (average in 5 animals; %/g) | | | | | |
|---|---|---|---|---|---|
| | Time after administration (hours) | | | | |
| | 0.25 | 0.5 | 1 | 2 | 3 |
| Blood | 7.79 | 6.97 | 6.33 | 5.47 | 5.07 |
| Liver | 1.39 | 1.43 | 1.38 | 1.20 | 1.43 |
| Spleen | 0.83 | 0.88 | 0.90 | 0.64 | 0.84 |
| Lung | 1.49 | 1.40 | 1.25 | 0.95 | 1.16 |
| Kidneys | 1.64 | 2.00 | 2.16 | 2.44 | 2.69 |
| Heart | 1.69 | 1.35 | 1.60 | 1.00 | 0.97 |
| Stomach | 0.40 | 0.70 | 0.68 | 0.74 | 0.92 |
| Small intestine | 0.40 | 0.56 | 0.62 | 0.75 | 0.97 |
| Large intestine | 0.18 | 0.15 | 0.18 | 0.17 | 0.23 |

From the results in Examples 10 and 11, it is understood that the $^{99m}$Tc-labeled, human serum albumin-combined BMTS can maintain a remarkably high blood level for a long period of time in comparison with conventional $^{99m}$Tc-labeled, human serum albumin and conventional $^{131}$I-labeled, human serum albumin. It is also understood that the $^{99m}$Tc-labeled, human serum albumin-combined BMTS is quite stable in a living body and gives a relatively low radioactivity at various organs in comparison with the blood level. Thus, the $^{99m}$Tc-labeled, human serum albumin-combined BMTS is quite suitable for the use in nuclear medical diagnosis aiming at recording, dynamic study and quantitative measurement of the blood circulation system.

EXAMPLE 12

Properties of $^{67}$Ga-labeled, human serum albumin-combined BETS:

In order to examine the labeling efficiency of the $^{67}$Ga-labeled, human serum albumin-combined BETS obtained in Example 7, it was subjected to electrophoresis (1.7 mA/cm; 15 minutes) using a Veronal-Veronal Na solution (pH 8.6) as a developing solvent and a cellulose acetate membrane as an electrophoretic membrane, and scanning was effected by the use of a radiochromato-scanner. The radioactivity was recognized as a single peak at the locus 1.8 cm distant from the original line to the positive side. This locus was the same as that of the coloring band of human seum albumin with Ponceau 3R.

From the above results, it may be said that the $^{67}$Ga-labeled, human serum albumin-combined BETS obtained in Example 7 has a labeling efficiency of nearly 100%, and its electric charge is substantially the same as that of human serum albumin.

EXAMPLE 13

Properties of $^{111}$In-labeled, urokinase-combined BMTS:

The enzymatic activity of the $^{111}$In-labeled, urokinase-combined BMTS was measured by the ester decomposition process using N-α-acetyl-L-lysine methyl ester to be 98% based on purified urokinase as the starting material.

From the above results, it may be said that the $^{111}$In-labeled, urokinase-combined BMTS retains substantially the enzymatic activity of the starting purified urokinase and shows no material difference from urokinase itself in the behavior in a living body.

EXAMPLE 14

Stability of human serum albumin-combined BMTS:

The human serum albumin-combined BMTS (solution) obtained in Example 3 was stored in a refrigerator at 4 to 8° C. for 30 days and then treated with $^{99m}$Tc according to the procedure as in Example 6 to give an aqueous solution containing the $^{99m}$Tc-labeled, human serum albumin-combined BMTS. With this solution, thin layer chromatography and electrophoresis were carried out according to the procedure as in Example 9 and also behaviors in rats were examined according to the procedure as in Example 11. The results were substantially the same as in Examples 9 and 11. Thus, it may be said that no material change is produced in the human serum albumin-combined BMTS by the storage for 30 days.

EXAMPLE 15

Stability of human serum albumin-combined BETS:

The human serum albumin-combined BETS (lyophilized powder) obtained in Example 4 was stored in a refrigerator at 4 to 8° C. for 30 days and then treated with $^{67}$Ga according to the procedure as in Example 7 to give an aqueous solution containing the $^{67}$Ga-labeled, human serum albumin-combined BETS. With this solution, electrophoresis was carried out according to the procedure as in Example 12. The radioactivity was recognized as a single peak, and its locus was confirmed to be the same as that of human serum albumin by coloring with Ponceau 3R. Thus, it may be said that no material change is produced in the human serum albumin-combined BETS by the storage for 30 days.

EXAMPLE 16

Stability of $^{99m}$Tc-labeled, human serum albumin-combined BMTS:

An aqueous solution containing the $^{99m}$Tc-labeled, human serum albumin-combined BMTS obtained in Example 6 was stored at room temperature (24°–27° C.) for 36 hours. With this solution, thin layer chromatography and electrophoresis were carried out according to the procedure as in Example 9 and also behaviors in rats were examined according to the procedure as in Example 11. The results were substantially the same as in Examples 9 and 11. Thus, it may be said that no material change is produced in the $^{99m}$Tc-labeled, human serum albumin-combined BMTS by the storage of 36 hours.

EXAMPLE 17

Stability of $^{67}$Ga-labeled, human serum albumin-combined BETS:

An aqueous solution containing the $^{67}$Ga-labeled, human serum albumin-combined BETS obtained in Example 7 was stored at room temperature (24°–27° C.) for 72 hours. With this solution, electrophoresis was carried out according to the procedure as in Example 12. The radioactivity was recognized as a single peak, and its locus was confirmed to be substantially the same as that of human serum albumin by coloring with Ponceau 3R. Thus, it may be said that no material change is produced in the $^{67}$Ga-labeled, human serum albumin-combined BETS by the storage of 72 hours.

EXAMPLE 18

Toxicity of non-radioactive carriers:

The non-radioactive carriers obtained in Examples 3 to 5 (perfectly dissolved in 0.2 M acetate buffer in case of the non-radioactive carrier obtained in Example 4) were administered intravenously to groups of male and female rats of SD strain, each group consisting of 10 animals, at a dose of 1 ml per 100 grams of the body weight (corresponding to 400 times the expected dose to human beings) and also to groups of male and female mice of ICR strain, each group consisting of 10 animals, at a dose of 0.5 ml per 10 grams of the body weight (corresponding to 2000 times the expected dose to human beings). As the control, the same volume of a physiological saline solution as above was intravenously administered to the separate groups of the same animals as above.

The animals were fertilized for 10 days, and the variation in body weight during that period was recorded. No significant difference was recognized between the medicated groups and the control groups.

After 10 days from the administration, all the animals were sacrificed and subjected to observation of the abnormality in various organs. But, no abnormality was seen in any of the animals.

From the above results, it may be said that the toxicity of the non-radioactive carriers of the invention is extremely low.

EXAMPLE 19

Toxicity of the radioactive diagnostic agent:

The $^{99m}$Tc-labeled, human serum albumin-combined BMTS obtained in Example 6 was subjected to attenuation of the radioactivity to an appropriate extent, and the resultant product was subjected to test for toxicity in the same manner as in Example 18. No significant difference was recognized between the medicated groups and the control groups. In all the animals sacrificed after 10 days from the administration, no abnormality was observed in their organs. Thus, it may be said that the radioactive diagnostic agent of the invention does not produce any material toxicity in tested animals even when administered in such a large dose as corresponding to 300 to 1500 times the expected dose to human beings.

What is claimed is:

1. A physiologically active substance-combined compound comprising a compound of the formula:

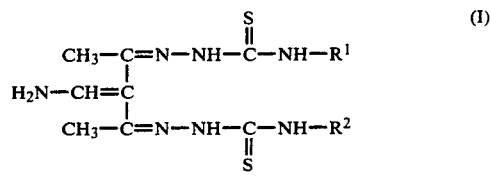

wherein $R^1$ and $R^2$ are each hydrogen, $C_1$-$C_3$ alkyl or phenyl, and a physiologically active substance bound therewith by a chemical bond.

2. The physiologically active substance-combined compound according to claim 1, wherein the chemical bond is a carbonamide linkage.

3. The physiologically active substance-combined compound according to claim 1, wherein the chemical bond is a pentamethylene linkage.

4. The physiologically active substance-combined compound according to claim 1, wherein the physiologically active substance is human serum albumin.

5. The physiologically active substance-combined compound according to claim 1, wherein the physiologically active substance is urokinase.

6. A radioactive metallic element-labeled, physiologically active substance-combined compound comprising the physiologically active substance-combined compound according to claim 1 and a radioactive metallic element bound with said compound through a chelating bond.

7. The radioactive metallic element-labeled, physiologically active substance-combined compound according to claim 9, wherein the radioactive metallic element is $^{99m}$Tc.

8. The radioactive metallic element-labeled, physiologically active substance-combined compound according to claim 9, wherein the radioactive metallic element is $^{67}$Ga.

9. The radioactive metallic element-labeled, physiologically active substance-combined compound according to claim 6, wherein the radioactive metallic element is $^{111}$In.

10. A process for preparing the physiologically active substance-combined compound according to claim 1, which comprises reacting a compound of the formula:

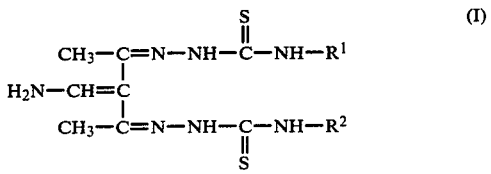

wherein $R^1$ and $R^2$ are each hydrogen, $C_1-C_3$ alkyl or phenyl, with a physiologically active substance.

11. The process according to claim 10, wherein the physiologically active substance has a carboxyl group, and the reaction proceeds between the amino group in the compound of the formula (I) and the carboxyl group in the physiologically active substance to form a carbonamide linkage.

12. The process according to claim 10, wherein the physiologically active substance has an amino group, and the reaction proceeds between the amino group in the compound of the formula (I) and the amino group in the physiologically active substance in the presence of glutaraldehyde, followed by reduction to form a pentamethylene linkage between the said amino groups.

13. A process for preparing a radioactive metallic element-labeled, physiologically active substance-combined compound which comprises contacting the physiologically active substance-combined compound according to claim 1 with a radioactive metallic element to combine them through a chelating bond.

14. The process according to claim 13, wherein the contact is carried out in an aqueous medium.

15. The process according to claim 13, wherein the contact is carried out in the presence of a reducing agent.

16. The physiologically active substance-combined compound according to claim 1, which is in the form of a solution.

17. The physiologically active substance-combined compound according to claim 1, which is in the form of lyophilized powder.

18. The physiologically active substance-combined compound according to claim 1, wherein $R^1$ and $R^2$ are each methyl.

19. The physiologically active substance-combined compound according to claim 1, wherein $R^1$ and $R^2$ are each ethyl.

* * * * *